United States Patent

Knowles et al.

[11] 4,167,568
[45] Sep. 11, 1979

[54] 8-AZAPURIN-6-ONE DERIVATIVES

[75] Inventors: Philip Knowles, Rayleigh; Edward Lunt, Westcliff-on-Sea; Stuart M. Marshall, Stanford-le-Hope; Roger E. Ford, Gidea Park, all of England

[73] Assignee: May & Baker Limited, Essex, England

[21] Appl. No.: 843,786

[22] Filed: Oct. 20, 1977

[30] Foreign Application Priority Data

Oct. 22, 1976 [GB] United Kingdom ............... 44008/76

[51] Int. Cl.² .................. C07D 487/04; A61K 31/41; A61K 31/505
[52] U.S. Cl. .................... 424/251; 260/153; 544/254
[58] Field of Search ........................ 544/254; 424/251; 260/153

[56] References Cited

U.S. PATENT DOCUMENTS

| | | | |
|---|---|---|---|
| 3,819,631 | 6/1974 | Broughton et al. | 544/254 |
| 3,933,822 | 1/1976 | Broughton et al. | 544/254 |
| 4,039,544 | 8/1977 | Broughton et al. | 544/254 |
| 4,052,390 | 10/1977 | Broughton et al. | 544/254 |

OTHER PUBLICATIONS

Herbst, "Graff, Essays in Biochemistry", 1956, John Wiley & Sons, Inc., N. Y., pp. 141-155.

Primary Examiner—Donald G. Daus
Assistant Examiner—James H. Turnipseed
Attorney, Agent, or Firm—Stevens, Davis, Miller & Mosher

[57] ABSTRACT

8-Azapurin-6-one derivatives of the formula:

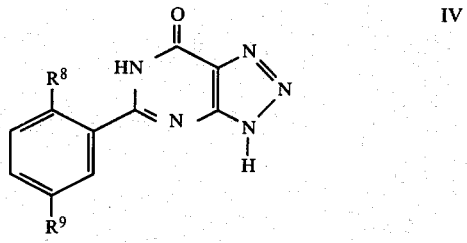

wherein $R^8$ represents alkoxy of from 1 to 6 carbon atoms, and $R^9$ represents cyano, or a group of the formula V, VI, VII, VIII or IX indicated below:

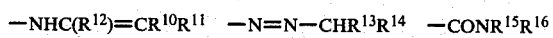

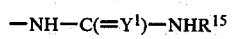

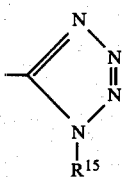

wherein $R^{10}$, $R_{13}$ and $R^{14}$ each represents cyano, or alkanoyl or alkoxycarbonyl of from 2 to 6 carbon atoms, $R^{11}$ represents hydrogen, cyano, or alkanoyl or alkoxycarbonyl of from 2 to 6 carbon atoms, $R^{12}$ represents hydrogen or, when $R^{11}$ represents hydrogen, $R^{12}$ represents alkyl of from 1 to 6 carbon atoms or alkoxycarbonyl of from 2 to 6 carbon atoms, or the pair of symbols $R^{11}$ and $R^{12}$ form together an alkylene chain of the formula —$(C_qH_{2q})$— wherein q is an integer from 3 to 6, $R^{15}$ and $R^{16}$ each represents hydrogen or alkyl of from 1 to 6 carbon atoms, and $Y^1$ represents oxygen or sulphur, are new compounds possessing pharmacological properties, in particular properties of value in the treatment of respiratory disorders such as allergic bronchial asthma.

30 Claims, No Drawings

8-AZAPURIN-6-ONE DERIVATIVES

This invention relates to new therapeutically useful 8-azapurin-6-one derivatives, to processes for their preparation and to pharmaceutical compositions containing them.

In the specification of British Pat. No. 1,338,235, as well as in the specifications of the equivalent U.S. Pat. Nos. 3,819,631 (granted June 25, 1974) and 3,987,160 (granted Oct. 19, 1976), there is described the class of 8-azapurin-6-one derivatives represented by the general formula:

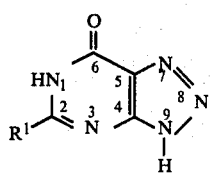

I

[wherein $R^1$ represents a phenyl or naphthyl group, which may optionally carry one or more substituents selected from halogen atoms and hydroxy, alkyl, phenylalkyl, alkoxy, alkenyloxy, alkynyloxy, alkoxyalkoxy, phenoxy, aralkoxy (e.g. phenylalkoxy), alkylthio, hydroxyalkyl, nitro, alkanesulphonyl, alkanoyl, alkoxycarbonyl, amino, trifluoromethyl and methylenedioxy groups and amino groups substituted by one or two groups selected from alkyl, phenyl, alkanoyl, alkanesulphonyl and arenesulphonyl (e.g. benzenesulphonyl) groups, or $R^1$ represents a straight- or branched-chain alkenyl or alkynyl group containing from 2 to 6 carbon atoms, a cycloalkyl group containing from 3 to 8 carbon atoms (e.g. cyclohexyl), a straight- or branched-chain alkyl group containing from 2 to 10 carbon atoms, or a straight- or branched-chain alkyl group containing from 1 to 10 carbon atoms carrying one or more substituents selected from halogen atoms, hydroxy groups, cycloalkyl groups containing from 3 to 8 carbon atoms, straight- or branched-chain alkoxy groups containing from 1 to 6 carbon atoms, and phenyl groups optionally carrying one or more substituents selected from halogen atoms and straight- or branched-chain alkyl and alkoxy groups containing from 1 to 6 carbon atoms, hydroxy groups, and phenylalkoxy (e.g. benzyloxy) groups in which the alkoxy moiety contains 1 to 6 carbon atoms] and pharmaceutically acceptable salts thereof.

In those Specifications it is stated that, when $R^1$ represents a substituted phenyl or substituted naphthyl group, alkyl groups and alkyl portions of phenylalkyl, alkylthio, aralkoxy, alkanoyl, alkanesulphonyl, hydroxyalkyl and alkoxycarbonyl substituents contain from 1 to 6 carbon atoms; each alkyl portion of an alkoxyalkoxy substituent contains from 1 to 6 carbon atoms; alkoxy substituents contain from 1 to 10 carbon atoms; alkenyloxy and alkynyloxy substituents contain 2 to 10 carbon atoms and alkyl and alkanoyl groups on amino substituents, and alkane portions of alkanesulphonyl groups on amino substituents, contain from 1 to 6 carbon atoms; phenoxy substituents, and phenyl groups on amino substituents, may carry one or more substituents selected from halogen (e.g. fluorine, chlorine or bromine) atoms and alkyl and alkoxy groups containing from 1 to 6 carbon atoms; aryl (e.g. phenyl) portions of aralkoxy substituents may carry one or more substituents selected from halogen (e.g. fluorine, chlorine or bromine) atoms, alkyl and alkoxy groups containing from 1 to 6 carbon atoms and nitro groups; and arene (e.g. benzene) portions of arenesulphonyl groups on amino substituents may carry one or more alkyl groups containing from 1 to 6 carbon atoms (e.g. methyl).

It is pointed out in the abovementioned specifications that the compounds of formula I exhibit tautomerism such that each of the hydrogen atoms depicted as residing on the nitrogen atoms in the 1- and 9-positions may reside on any of the nitrogen atoms in the 1-, 3-, 7-, 8- and 9-positions or on the oxygen atom connected to the carbon atom in the 6-position, and that all the forms thus described may be present to a greater or lesser degree and are in a state of dynamic equilibrium with each other. Furthermore, in certain cases the substituent $R^1$ contributes to optical and/or stereoisomerism. All such forms are embraced by the invention described in the aforementioned specifications.

In the specification of British Pat. No. 1,421,970, as well as in the specifications of the equivalent United States Patent Applications Ser. Nos. 478387 (U.S. Pat. No. 3,933,822—granted Jan. 20, 1976) and 574,870 (now U.S. Pat. No. 4,052,390, granted Oct. 4, 1977) divided therefrom, filed June 11, 1974 and May 6, 1975 respectively, there is described a class of 8-azapurin-6-one derivatives related to the compounds of formula I, namely the compounds of the general formula:

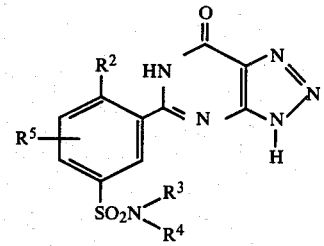

II

[wherein $R^2$ represents a hydroxy group, a straight- or branched-chain alkoxy or alkylthio group containing from 1 to 10 carbon atoms, $R^3$ represents a hydrogen atom, or a straight- or branched-chain alkyl, alkenyl or alkynyl group, each such group containing up to 10 carbon atoms, and may carry one or more substituents selected from hydroxy groups, phenyl groups and cycloalkyl groups containing from 3 to 8 carbon atoms, or $R^3$ represents a cycloalkyl group containing from 3 to 8 carbon atoms, or a phenyl group which may carry one or more substituents selected from alkyl and alkoxy groups containing from 1 to 6 carbon atoms, halogen (e.g. chlorine) atoms, and nitro and trifluoromethyl groups, and $R^4$ represents a hydrogen atom, or a straight- or branched-chain alkyl, alkenyl or alkynyl group, each such group containing up to 10 carbon atoms, and may carry one or more substituents selected from hydroxy groups, phenyl groups and cycloalkyl groups containing from 3 to 8 carbon atoms, or $R^4$ represents a cycloalkyl group containing from 3 to 8 carbon atoms, or the group $-NR^3R^4$ represents a 5-, 6- or 7-membered heterocyclic group which may contain besides the nitrogen atom one or more additional hetero atoms (e.g. nitrogen, oxygen or sulphur) and may be substituted by one or more straight- or branched-chain alkyl groups containing from 1 to 6 carbon atoms (e.g. piperidino, 1-pyrrolidinyl and morpholino), and $R^5$ represents a hydrogen atom or a methyl or ethyl group] and pharmaceutically acceptable salts thereof.

In the specification of Belgian Pat. No. 841181 and the equivalent U.S. Pat. No. 4,039,544 (granted Aug. 2, 1977), there is described another class of 8-azapurin-6-one derivatives related to the class of compounds of formula I and the class of compounds of formula II, namely the compounds of the general formula:

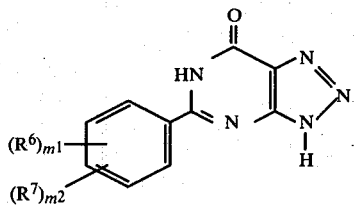

III

[wherein $R^6$ represents an alkylthio, alkylsulphinyl, alkylsulphonyl or alkoxycarbonyl group, $R^7$ represents a halogen atom, a hydroxy, alkyl, phenylalkyl, alkoxy, alkenyloxy, alkynyloxy, alkoxyalkoxy, phenoxy, aralkoxy (e.g. phenylalkoxy), hydroxyalkyl, alkanoyl, trifluoromethyl or methylenedioxy group or an amino groups substituted by two groups selected from alkyl, phenyl, alkanoyl, alkylsulphonyl and arylsulphonyl (e.g. phenylsulphonyl) groups or by one group selected from alkanoyl, alkylsulphonyl and arylsulphonyl (e.g. phenylsulphonyl) groups, $m^1$ represents an integer from 1 to 4 and $m^2$ represents an integer from 1 to 4, the sum of $m^1 + m^2$ being not greater than 5] and pharmaceutically acceptable salts thereof.

When the symbol $m^1$ represents an integer greater than one the substituents represented by the symbol $R^6$ may be different but are preferably identical. When the symbol $m^2$ represents an integer greater than one the substituents represented by the symbol $R^7$ may be identical or different.

In those specifications it is stated in relation to formula III that alkyl groups and alkyl portions of alkylthio, alkylsulphinyl, alkylsulphonyl, alkoxycarbonyl, phenylalkyl, aralkoxy, alkanoyl and hydroxyalkyl groups contain from 1 to 6 carbon atoms, each alkyl portion of an alkoxyalkoxy substituent contains from 1 to 6 carbon atoms; alkoxy groups contain from 1 to 10 carbon atoms; alkenyloxy and alkynyloxy substituents contain from 2 to 10 carbon atoms; phenoxy groups, and phenyl groups on amino substituents may carry one or more substituents selected from halogen (e.g. fluorine, chlorine or bromine) atoms, and alkyl and alkoxy groups containing from 1 to 6 carbon atoms; aryl (e.g. phenyl) portions of aralkoxy substituents may carry one or more substituents selected from halogen (e.g. fluorine, chlorine or bromine) atoms, and alkyl and alkoxy groups containing from 1 to 6 carbon atoms; and aryl (e.g. phenyl) portions of arylsulphonyl groups on amino substituents may carry one or more alkyl groups containing from 1 to 6 carbon atoms (e.g. methyl). The carbon atoms in the alkyl, alkoxy, alkanoyl, alkenyloxy and alkynyloxy groups or moieties may be in a straight- or branched-chain.

The 8-azapurin-6-one derivatives of general formula I, general formula II and general formula III described in the aforementioned specifications possess valuable pharmacological properties, in particular properties of value in the treatment of respiratory disorders manifested by the interaction of tissue-fixed antibodies with specific antigens, such as allergic bronchial asthma.

It has now been found as a result of further extensive research and experimentation that, when $R^1$ in general formula I represents a phenyl group substituted in the meta-position by a substituent selected from certain nitrogen-containing groups as hereinafter specified, the hitherto unknown compounds, which form a class distinct from the compounds of general formulae I, II and III, exhibit similar valuable pharmacological properties to the 8-azapurin-6-one derivatives of general formulae I, II and III with, in some aspects of their properties, an improvement.

The present invention thus provides compounds of the general formula:

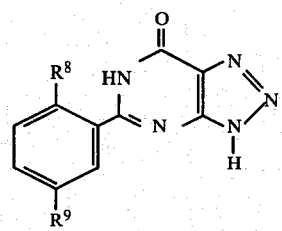

IV

[wherein $R^8$ represents a straight- or branched-chain alkoxy group containing from 1 to 6 carbon atoms, for example a methoxy or propoxy group, and $R^9$ represents a cyano group or a group of the general formula V, VI, VII, VIII or IX indicated below:

$$-NHC(R^{12})=CR^{10}R^{11} \quad -N=N-CHR^{13}R^{14} \quad -CONR^{15}R^{16}$$

V            VI            VII

$$-NH-C(=Y^1)-NHR^{15}$$

VIII

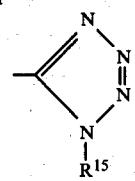

IX

[wherein $R^{10}$, $R^{13}$ and $R^{14}$, which may be the same or different, each represents a cyano group or a straight- or branched-chain alkanoyl or alkoxycarbonyl group containing from 2 to 6 carbon atoms, for example an acetyl, methoxycarbonyl or ethoxycarbonyl group, $R^{11}$ represents a hydrogen atom, a cyano group, or a straight- or branched-chain alkanoyl or alkoxycarbonyl group containing from 2 to 6 carbon atoms, for example an acetyl, methoxycarbonyl or ethoxycarbonyl group, $R^{12}$ represents a hydrogen atom or, when $R^{11}$ represents a hydrogen atom, $R^{12}$ represents a straight- or branched-chain alkyl group containing from 1 to 6 carbon atoms, e.g. methyl, or straight- or branched-chain alkoxycarbonyl group containing from 2 to 6 carbon atoms, e.g. methoxycarbonyl, or the pair of symbols $R^{11}$ and $R^{12}$ may form together a straight or branched alkylene chain of the formula -$(C_qH_{2q})$- wherein q is an integer from 3 to 6, for example a trimethylene group, $R^{15}$ and $R^{16}$, which may be the same or different, each represents a hydrogen atom or a straight- or branched-chain alkyl group containing from 1 to 6 carbon atoms, for example a methyl, ethyl, propyl, isopropyl or t-butyl group, and $Y^1$ represents an oxygen or sulphur atom] and pharmaceutically acceptable salts thereof.

Compounds of formula IV wherein $R^9$ represents a group of formula V wherein $R^{10}$ and $R^{11}$ are different exhibit geometric isomerism. Furthermore the groups represented by $R^8$ and $R^9$ may exhibit optical isomerism.

The present invention includes all tautomers, geometrical isomers, and optical isomers of formula IV, and mixtures thereof.

Individual compounds of formula IV of particular importance include the following:

| | |
|---|---|
| 2-[5-{2,2-bis(ethoxycarbonyl)vinylamino}-2-propoxyphenyl]-8-azapurin-6-one; | A |
| 2-[5-(2,2-diacetylvinylamino)-2-propoxyphenyl]-8-azapurin-6-one; | B |
| 2-[5-(2-cyano-2-ethoxycarbonylvinylamino)-2-propoxyphenyl]-8-azapurin-6-one (mixture of 60% Z isomer and 40% E isomer); | C |
| 2-[5-(2-acetyl-2-ethoxycarbonylvinylamino)-2-propoxyphenyl]-8-azapurin-6-one (mixture of Z and E isomers); | D |
| 2-[5-{2,2-bis(ethoxycarbonyl)vinylamino}-2-methoxyphenyl]-8-azapurin-6-one; | E |
| 2-[5-(2,2-diacetylvinylamino)-2-methoxyphenyl]-8-azapurin-6-one; | F |
| 2-[5-{2,2-bis(methoxycarbonyl)vinylamino}-2-propoxyphenyl]-8-azapurin-6-one; | G |
| (Z)-2-[5-{1,2-bis(methoxycarbonyl)vinylamino}-2-propoxyphenyl]-8-azapurin-6-one; | H |
| 2-[5-(1-acetylprop-1-en-2-ylamino)-2-methoxyphenyl]-8-azapurin-6-one; | I |
| 2-[5-(2,4-dioxopent-3-ylazo)-2-propoxyphenyl]-8-azapurin-6-one; | J |
| 2-[5-{bis(ethoxycarbonyl)methylazo}-2-propoxyphenyl]-8-azapurin-6-one; | K |
| 2-(5-cyano-2-propoxyphenyl)-8-azapurin-6-one; | L |
| 2-(5-carbamoyl-2-propoxyphenyl)-8-azapurin-6-one; | M |
| 2-(5-N-t-butylcarbamoyl-2-propoxyphenyl)-8-azapurin-6-one; | N |
| 2-[2-propoxy-5-(3-isopropylureido)phenyl]-8-azapurin-6-one; | O |
| 2-[2-propoxy-5-(3-propylureido)phenyl]-8-azapurin-6-one; | P |
| 2-[5-(3-methyl-2-thioureido)-2-propoxyphenyl]-8-azapurin-6-one; | Q |
| 2-[2-propoxy-5-(3-propyl-2-thioureido)phenyl]-8-azapurin-6-one; | R |
| 2-(2-propoxy-5-ureidophenyl)-8-azapurin-6-one; | S |
| 2-[2-propoxy-5-(tetrazol-5-yl)phenyl]-8-azapurin-6-one; | T |
| 2-[5-(2-ethoxycarbonylcyclopent-1-enylamino)-2-propoxyphenyl]-8-azapurin-6-one; | U |
| 2-(5-N,N-diethylcarbamoyl-2-propoxyphenyl)-8-azapurin-6-one; and | V |
| 2-(5-N-methyl-N-isopropylcarbamoyl-2-propoxyphenyl)-8-azapurin-6-one; | W | and their pharmaceutically acceptable salts.

The letters of the alphabet A to W are assigned to the compounds for easy reference later in the specification, for example in the following Tables.

The pharmacological properties of the compounds of formula IV, useful in the treatment of respiratory disorders manifested by the interaction of tissue-fixed antibodies with specific antigens, such as allergic bronchial asthma, have been demonstrated in the following tests.

The codes RCA, RCB and RCC, used in the expression of test results, refer to the reference compounds 2-(2-propoxyphenyl)-8-azapurin-6-one (RCA), a typical compound of formula I, and 2-[2-propoxy-5-(N-methyl-N-isopropylsulphamoyl)-phenyl]-8-azapurin-6-one (RCB), a typical compound of formula II, and 2-(2-propoxy-5-propylsulphonylphenyl)-8-azapurin-6-one (RCC), a typical compound of formula III, respectively.

A.1. Passive cutaneous anaphylactic reaction test in rats (intravenous)

By comparing the compounds of the present invention with reference compound RCA in a test similar to that described in aforementioned U.S. Pat. No. 3819631, the compounds were found to possess the relative activities shown below in Table I.

TABLE I

| Compound | A | B | C | D | E | F | G |
|---|---|---|---|---|---|---|---|
| Relative Activity | 5 | 50 | 10 | 10 | 5 | 5 | 50 |
| Compound | H | I | J | K | L | M | N |
| Relative Activity | 15 | 5 | 10 | 2.5 | 1 | 10 | 50 |
| Compound | O | P | Q | R | S | T | U |
| Relative Activity | 30 | 2 | 10 | 0.2 | 5 | 2 | 5 |
| Compound | V | W | RCA | | | | |
| Relative Activity | 3 | 5 | 1 | | | | |

Thus, the great majority of the compounds tested are substantially more active than reference compound RCA in this test.

A.2. Passive cutaneous anaphylactic reaction test in rats (oral)

By comparing test compounds A and C with reference compounds RCB and RCC in a test similar to that described in U.S. Pat. No. 3,819,631, it was found that reference compounds RCB and RCC are approximately equiactive orally and that test compound A was over 5 times as active orally as reference compounds RCB and RCC and that test compound C was over 2.5 times as active orally as reference compounds RCB and RCC.

The utility of the compounds of formula IV is enhanced by the fact that they are only of very low toxicity to mammals, demonstrated by the following tests.

T.1. Acute oral toxicity in mice

Mice were each treated orally with one of the compounds of formula IV, and they were observed during the next 3 days. The LD50 figures obtained (doses lethal to 50% of mice tested) are shown in Table II, expressed in mg/kg animal body weight.

TABLE II

| Compound | E | J | N | O | R |
|---|---|---|---|---|---|
| LD50 | >1000 | >1000 | >1000 | >1000 | >1000 |

The symbol ">" means "greater than".

No deaths occurred even at the highest dose used, 1000 mg/kg.

T.2. Acute intravenous toxicity in mice

Mice were each treated intravenously with an aqueous solution of the triethanolamine salt of one of the compounds of formula IV, and they were observed during the next 7 days. The LD50 figures obtained (doses lethal to 50% of mice tested) are shown below in Table III, expressed in mg/kg animal body weight.

The aqueous solutions used were prepared as follows:- A mixture of the test compound and water was treated gradually with triethanolamine until complete solution occurred. The solution was then diluted with water to a concentration of either 1% w/v or 2% w/v. Various volumes of these solutions were then administered to the mice.

TABLE III

| Compound | B | C | D | E | G | H | I | K | U |
|---|---|---|---|---|---|---|---|---|---|
| Concentration of test solution (% w/v) | 1 | 2 | 2 | 1 | 2 | 2 | 1 | 2 | 2 |
| LD50 | 350 | 290 | 270 | 320 | 280 | 410 | 470 | 255 | 220 |

T.3. Emetic activity

The emetic activity in dogs of test compound A was compared with that of the reference compound RCA.

Four beagle dogs, each of approximately 12 kg body weight, were starved overnight and then were given orally gelatine capsules containing either test compound A or RCA. The dogs were observed for at least 2.5 hours after dosing.

Reference compound RCA caused vomiting in all four dogs, dosed at 100 mg/kg animal body weight.

However, test compound A caused vomiting in none of the four dogs, dosed at 200 mg/kg animal body weight.

The same four animals were used to test both compounds.

According to features of the present invention, compounds of formula IV are prepared by the application or adaptation of known methods, for example (1) Compounds of formula IV wherein $R^9$ represents a cyano group are prepared by the reaction of a diazonium salt which may be represented by the general formula:-

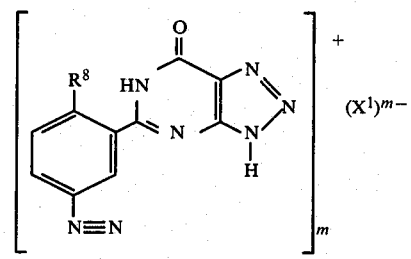

X (wherein $R^8$ is as hereinbefore defined, and $(X^1)^{m-}$ represents the anion of a strong inorganic acid, preferably the chloride ion, and m is the basicity of that acid) with cyanide ions in the presence of a cuprous salt, for example by reaction with potassium cyanide in the presence of cuprous cyanide, in aqueous conditions and preferably at a temperature between 25° and 80° C.

The compounds of formula X are usually prepared in situ by the action of a strong inorganic acid, preferably hydrochloric acid, and an alkali metal nitrite, e.g. sodium nitrite or potassium nitrite, on compounds of the general formula:-

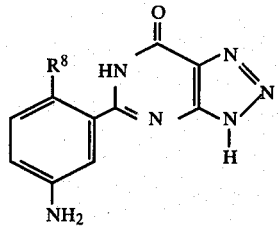

XI (wherein $R^8$ is as hereinbefore defined) in aqueous conditions and at a temperature between $-10°$ C. and $+30°$ C. Alternatively an acid solution salt of an amine of formula XI may be treated with an alkali metal nitrite in aqueous conditions and between $-10°$ C. and $+30°$ C.

(2) Compounds of formula IV wherein $R^9$ represents a group of formula V are prepared by the reaction of compounds of formula XI with compounds of the general formulae XII or XIII:-

| $R^{17}OCR^{12}=CR^{10}R^{11}$ | $O=CR^{12}-CHR^{10}R^{11}$ |
|---|---|
| XII | XIII |

(wherein $R^{10}$, $R^{11}$ and $R^{12}$ are as hereinbefore defined and $R^{17}$ represents a straight- or branched-chain alkyl group containing from 1 to 4 carbon atoms, preferably an ethyl group) at a temperature between 25° C. and 150° C. and optionally in a dry organic solvent, e.g. dry sulpholane.

(3) Compounds of formula IV wherein $R^9$ represents a group of formula V wherein $R^{11}$ represents a hydrogen atom and $R^{10}$ and $R^{12}$ represent identical alkoxycarbonyl groups, $R^8$ being as hereinbefore defined, are prepared by the reaction of a compound of formula XI with a compound of the general formula:

$$R^{18}OOC-C\equiv C-COOR^{18} \qquad XIV$$

(wherein the symbols $R^{18}$ both represent identical straight- or branched-chain alkyl groups, each containing from 1 to 5 carbon atoms) at a temperature between 25° and 150° C. and preferably in the presence of a dry organic solvent, e.g. dry methanol.

(4) Compounds of formula IV wherein $R^9$ represents a group of formula VI are prepared by the reaction of a compound of formula X (preferably prepared in situ) with a compound of the general formula:

$$R^{13}\text{-CH}_2\text{-}R^{14} \qquad XV$$

(wherein $R^{13}$ and $R^{14}$ are as hereinbefore defined), preferably in an aqueous alkanolic medium, e.g. aqueous ethanol, and at a temperature between $-10°$ C. and $+30°$ C. and in the presence of a suitable buffer such as sodium acetate.

(5) Compounds of formula IV wherein $R^9$ represents a group of formula V or VI wherein one or more of the symbols $R^{10}$, $R^{11}$ and $R^{12}$, or $R^{13}$ and $R^{14}$ represents an alkoxycarbonyl group of the general formula:

$$-COOR^{18} \qquad XVI$$

(wherein $R^{18}$ is as hereinbefore defined) are prepared from a corresponding compound of formula IV wherein said symbol or symbols selected from $R^{10}$, $R^{11}$ and $R^{12}$, or $R^{13}$ and $R^{14}$ represents a different alkoxycarbonyl group, by means of a transesterification reaction.

The reaction may be carried out in the presence of the appropriate alkali metal alkoxide of the general formula:

$$M^1OR^{18} \qquad XVII$$

(wherein $R^{18}$ is as hereinbefore defined and $M^1$ represents an alkali metal, e.g. sodium or potassium, atom) and in a medium comprising an excess of the appropriate alkanol of the general formula:

$$R^{18}OH \qquad XVIII$$

(wherein $R^{18}$ is as hereinbefore defined) at a temperature between 25° C. and 120° C.

(6) Compounds of formula IV wherein $R^9$ represents a group of formula VII are prepared by reaction of a carboxylic acid of the general formula:-

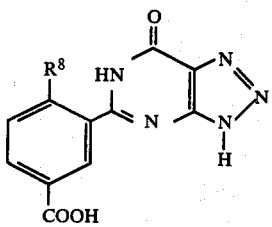

XIX (wherein $R^8$ is as hereinbefore defined), or an acid halide, preferably the acid chloride, thereof, with a compound of the general formula:

$$HNR^{15}R^{16} \qquad XX$$

wherein $R^{15}$ and $R^{16}$ are as hereinbefore defined.

The reaction using the carboxylic acid of formula XIX may be carried out in an organic solvent, e.g. pyridine, and in the presence of a condensing agent, e.g. dicyclohexylcarbodiimide, preferably at a temperature between 25° C. and 120° C.

The reaction using the acid halide of the carboxylic acid of formula XIX may be carried out in an organic solvent, e.g. dimethyl formamide, preferably at a temperature between 0° C. and 60° C. If desired, the reaction of the acid halide may be carried out in the presence of an acid-binding agent, which may be an excess of the amine of formula XX or may be a tertiary amine, e.g. triethylamine.

Carboxylic acids of formula XIX may be converted to their acid halides by the application or adaptation of known methods. For example, acid chlorides may be prepared by the action of thionyl chloride, preferably in an organic solvent, e.g. dimethylformamide, preferably at a temperature between 0° C. Advantageously the acid halide is prepared in situ before the addition of the compound of formula XX to the reaction mixture.

(7) Compounds of formula IV wherein $R^9$ represents a carbamoyl group (-$CONH_2$) are prepared by the hydrolysis of compounds of formula IV wherein $R^9$ represents a cyano group, by the application or adaptation of known methods, for example by the action of concentrated sulphuric acid.

(8) Compounds of formula IV wherein $R^9$ represents a group of formula VIII wherein $R^{15}$ represents an alkyl group are prepared by the reaction of compounds of formula XI with compounds of the general formula:

$$R^{19}-N=C=Y^1 \qquad XXI$$

wherein $Y^1$ is as hereinbefore defined and $R^{19}$ represents a straight- or branched-chain alkyl group containing from 1 to 6 carbon atoms. The reaction may be carried out in an organic solvent, e.g. N-methylpyrrolid-2-one, preferably at a temperature between 0° C. and 150° C.

(9) Compounds of formula IV wherein $R^9$ represents a ureido group ($NH_2.CO.NH$-) are prepared by the reaction of a compound of formula XI with urea, preferably at an elevated temperature, e.g. between 100° and 200° C.

(10) Compounds of formula IV wherein $R^9$ represents a thioureido group ($NH_2.CS.NH$-) are prepared by the reaction of a corresponding compound of formula IV wherein $R^9$ represents a ureido group with phosphorus pentasulphide ($P_4S_{10}$). The reaction may be carried out at ambient or elevated temperature and in an inert solvent.

(11) Compounds of formula IV wherein $R^9$ represents a group of formula IX are prepared by the reaction of a compound of formula IV wherein $R^9$ represents a cyano group with an appropriate azide reagent, preferably in an organic solvent, e.g. N-methylpyrrolid-2-one, preferably at a temperature between 0° C. and 120° C.

When $R^{15}$ in the desired product of formula IV represents a hydrogen atom, the appropriate azide reagent may be hydrazoic acid, ammonium azide, aluminium azide, pyridinium azide, or an alkali metal azide, e.g. sodium azide.

When $R^{15}$ in the desired product of formula IV represents an alkyl group, the appropriate azide reagent is an alkyl azide of the general formula:

$$R^{19}N_3 \qquad XXII$$

(wherein $R^{19}$ is as hereinbefore defined).

Compounds of formula XI are within general formula I and may be prepared by the application or adaptation of methods described in the aforementioned British Patent specification No. 1,338,235 and U.S. Pat. No. 3,819,631.

Compounds of formula XIX may be prepared by the oxidation of compounds of the general formula:-

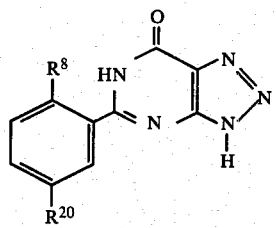

XXIII (wherein $R^{20}$ represents a lower alkyl group, preferably a methyl group, and $R^8$ is as hereinbefore defined), for example by the action of an alkali metal permanganate (e.g. sodium permanganate or potassium permanganate), preferably in the presence of an aqueous alkali metal hydroxide (e.g. sodium hydroxide) and at an elevated temperature (e.g. 60°–100° C.).

The present invention includes pharmaceutically acceptable salts of compounds of formula IV with pharmaceutically acceptable bases. By the term "pharmaceutically acceptable salts" is meant salts the cations of which are relatively innocuous to the animal organism when used in therapeutic doses so that the beneficial pharmacological properties of the parent compounds of general formula IV are not vitiated by side effects ascribable to those cations. Suitable salts include the salts of amines, preferably tertiary amines, known in the art to be pharmaceutically acceptable, e.g. choline, diethanolamine, triethanolamine, and triethylamine.

According to a further feature of the present invention, pharmaceutically acceptable amine salts may be prepared by the reaction together of a compound of formula IV and the appropriate amine, that is to say, an amine as described immediately hereinbefore, for example at an elevated temperature, with or without an appropriate solvent, e.g. an anhydrous alkanol containing from 1 to 5 carbon atoms, optionally followed by recrystallisation of the salt from an appropriate solvent, for example a hydroxylic solvent, e.g. an alkanol containing from 1 to 5 carbon atoms, of the salt so formed.

It is to be understood that, where in this specification reference is made to compounds of formula IV, it is intended to refer also, where the context so permits, to the said salts of the compounds of formula IV.

By the term "known methods" is meant methods heretofore used or described in the literature.

The following Examples illustrate the preparation of the new compounds of the present invention.

The Reference Examples following thereafter illustrate the preparation of starting materials used in the Examples.

EXAMPLE 1

Compounds A,B,C,D,E and F

A suspension of 2-(5-amino-2-propoxyphenyl)-8-azapurin-6-one (1.43 g) in dry sulpholane (15 ml) was treated with diethyl ethoxymethylenemalonate (1.25 g). The mixture was then stirred at 140° C. for one hour, under a slight vacuum in order to remove ethanol. After cooling, the mixture was poured with stirring into dilute hydrochloric acid (150 ml; 2 N), to give a buff-coloured gum which, on scratching, crystallised. Recrystallisation twice from a mixture of dimethylformamide and water, with the aid of charcoal, gave 2-[5-{2,2-bis(ethoxycarbonyl)-vinylamino}-2-propoxyphenyl]-8-azapurin-6-one (1.3 g), m.p. 226°-227° C.

By proceeding in a similar manner, but replacing the diethyl ethoxymethylenemalonate used as a starting material by the appropriate quantities of 3-ethoxymethylenepentan-2,4-dione, of a mixture of the Z and E isomers of ethyl-2-cyano-3-ethoxyacrylate, and of a mixture of the Z and E isomers of ethyl 2-acetyl-3-ethoxyacrylate, respectively, there were prepared 2-[5-(2,2-diacetylvinylamino)-2-propoxyphenyl]-8-azapurin-6-one, m.p. 278°-280° C. (with decomposition), a 60:40 mixture of the Z and E isomers of 2-[5-(2-cyano-2-ethoxycarbonylvinylamino)-2-propoxyphenyl]-8-azapurin-6-one, m.p. 268°-270° C. (with decomposition), and a mixture of the Z and E isomers of 2-[5-(2-acetyl-2-ethoxycarbonylvinylamino)-2-propoxyphenyl]-8-azapurin-6-one, m.p. 206°-207° C. (with decomposition).

By again proceeding in a similar manner, but replacing the 2-(5-amino-2-propoxyphenyl)-8-azapurin-6-one used as a starting material by the appropriate quantity of 2-(5-amino-2-methoxyphenyl)-8-azapurin-6-one (prepared as described in the specifications of British Pat. No. 1,338,235 and U.S. Pat. No. 3,819,631), there was prepared 2-[5-{2,2-bis(ethoxycarbonyl)vinylamino}-2-methoxyphenyl]-8-azapurin-6-one, m.p. 257°-258° C. (with decomposition).

By again proceeding in a similar manner, but using as starting materials the appropriate quantities of 2-(5-amino-2-methoxyphenyl)-8-azapurin-6-one and 3-ethoxymethylenepentan-2,4-dione, there was prepared 2-[5-(2,2-diacetylvinylamino)-2-methoxyphenyl]-8-azapurin-6-one, m.p. 291°-293° C. (with decomposition).

EXAMPLE 2

Compound G

Dry methanol (50 ml) was treated with sodium (0.4 g) and, after evolution of hydrogen had ceased, 2-[5-{2,2-bis(ethoxycarbonyl)vinylamino}-2-propoxyphenyl[-8-azapurin-6-one (2.0 g; prepared as described in Example 1) was added to the solution. The mixture was stirred and heated at reflux for 2 hours and was then cooled and poured into dilute hydrochloric acid (2 N). The precipitated solid was filtered off, washed with water, and recrystallised from a mixture of dimethylformamide and water to give 2-[5-{2,2-bis(methoxycarbonyl)-vinylamino}-2-propoxyphenyl]-8-azapurin-6-one (1.6g), m.p. 247°-250° C. (with decomposition).

EXAMPLE 3

Compound H 2-(5-Amino-2-propoxyphenyl)-8-azapurin-6-one (1.43 g), dimethyl acetylenedicarboxylate (0.85 g) and dry methanol (20 ml) were stirred and heated together at reflux for 5 hours. The resulting mixture was then cooled in an ice-bath for 30 minutes and the resulting yellow crystalline precipitate was filtered off and recrystallised from ethanol to give (Z)-2-[5-{1,2-bis(methoxycarbonyl)vinylamino}-2-propoxyphenyl]-8-azapurin-6-one (1.0 g), m.p. 199°-200° C. (with decomposition).

EXAMPLE 4

Compound I

A stirred suspension of 2-(5-amino-2-methoxyphenyl)-8-azapurin-6-one (1.34 g) in acetylacetone (15 ml) was heated at reflux for one hour. The mixture was then cooled and poured into diethyl ether (100 ml). The precipitated solid was filtered off and recrystallised twice from ethanol with the aid of charcoal to give 2-[5-(1-acetylprop-1-en-2-ylamino)-2-methoxyphenyl]-8-azapurin-6-one (1.2 g), m.p. 239°-240° C. (with decomposition).

EXAMPLE 5

Compounds J and K 2-(5-Amino-2-propoxyphenyl)-8-azapurin-6-one (1.5 g) was dissolved in a hot mixture of concentrated hydrochloric acid (4 ml) and water (20 ml). The solution was then cooled to 0° C. to give a suspension of 2-(5-amino-2-propoxyphenyl)-8-azapurin-6-one hydrochloride. The stirred suspension was treated with a solution of sodium nitrite (0.5 g) in water (2 ml) during 10 minutes. After stirring for one hour at 0° C., a sufficient quantity of sulphamic acid was added to decompose the excess of nitrous acid. The resulting ice-cold solution was then added, dropwise, to a stirred mixture of acetylacetone (2 ml), ethanol (20 ml), water (10 ml) and sodium acetate (5 g) at 0° C. during 30 minutes. After a further 30 minutes, the thick yellow mixture was filtered, and the precipitate was washed with water and sucked dry. Recrystallisation from a mixture of dimethylformamide and methanol gave 2-[5-(2,4dioxopent-3-ylazo)-2-propoxyphenyl]-8-azapurin-6-one (1.4 g), m.p. 288°-290° C. (with decomposition).

By proceeding in a similar manner but replacing the acetylacetone used as a starting material by the appropriate quantity of diethyl malonate, there was prepared 2-[5-{bis-(ethoxycarbonyl)methylazo}-2-propoxyphenyl]-8-azapurin-6-one, m.p. 201°–202° C. (with decomposition) (recrystallised from ethanol).

EXAMPLE 6

Compound L

A stirred mixture of 2-(5-amino-2-propoxyphenyl)-8-azapurin-6-one (2.0 g), concentrated hydrochloric acid (4 ml) and water (8 ml) was slowly treated with a solution of sodium nitrite (0.7 g) in water (3 ml) whilst maintaining the temperature at 5° C. The mixture was stirred for a further 90 minutes at 5° C., and then the excess of nitrous acid was removed by the addition of sulphamic acid. The solution was added during 15 minutes to a stirred mixture of potassium cyanide (4.6 g), cuprous cyanide (6 g) and water (60 ml), of which the initial temperature was 60°–70° C., controlling troublesome frothing by treatment with a small quantity of amyl alcohol. The resulting brown suspension was stirred at 70°–80° C. for a further 15 minutes, and it was then cooled. The insoluble brown solid was filtered off, washed with water and then heated at 70°–80° C. for 2 hours with a stirred mixture of hydrated ferric chloride (25 g), water (100 ml) and concentrated hydrochloric acid (16 ml). The mixture was left to stand in the refrigerator overnight. The mixture was then filtered and the resulting solid was washed with dilute hydrochloric acid (2 N) and then with water. The solid was then dissolved in dilute aqueous ammonia solution (50 ml; 2 N). The resulting solution was acidified by treatment with concentrated hydrochloric acid and the solid which separated was filtered off, washed with water, and crystallised from isopropanol to give 2-(5-cyano-2-propoxyphenyl)-8-azapurin-6-one (0.8 g), in the form of colourless prisms (containing one molecule of isopropanol as solvate), m.p. 216°–219° C. The corresponding hemihydrate, m.p. 221°–223.5° C. (with decomposition), was obtained by means of the dissolution of this material in dilute aqueous ammonia solution, precipitation by the addition of concentrated hydrochloric acid, and filtration of the solid obtained.

EXAMPLE 7

Compound M 2-(5-Cyano-2-propoxyphenyl)-8-azapurin-6-one (2.0 g; prepared as described in Example 6) was carefully added with stirring to concentrated sulphuric acid (20 ml) during 10 minutes. The resulting solution was allowed to stand at room temperature for 3 hours, and then it was poured into iced water (100 ml) and the mixture was allowed to stand for 2 hours. The resulting solid was then filtered off and dissolved in aqueous sodium carbonate solution (2 N; 50 ml). This solution was treated with charcoal, filtered, and acidified by the addition of concentrated hydrochloric acid, and the resulting white solid was recrystallised from dimethylformamide. The recrystallised solid was dissolved in aqueous sodium carbonate solution (2 N; 50 ml) and the solution was acidified by the addition of concentrated hydrochloric acid and the resulting solid was filtered off to give 2-(5-carbamoyl-2-propoxyphenyl)-8-azapurin-6-one (0.9 g), m.p. 273°–275° C. (with decomposition).

EXAMPLE 8

Compound N

A solution of 2-(5-carboxy-2-propoxyphenyl)-8-azapurin-6-one (7.0 g) in dry pyridine (140 ml) was treated with dicyclohexylcarbodiimide (9.8 g) and the mixture was stirred at room temperature for 90 minutes. Dry tert-butylamine (35 ml) was then added, and the stirred mixture was heated at 60° C. for 8 hours, and was then allowed to stand at room temperature for 2 days. The pyridine was removed in vacuo and the residue was treated with an aqueous solution of tert-butylamine (10% w/v; 200 ml) and heated at reflux for 30 minutes. When the mixture had cooled to room temperature, the precipitated dicyclohexylurea was filtered off. The filtrate was acidified by treatment with concentrated hydrochloric acid and the resulting precipitate was recrystallised from methanol and dried at 185° C./10 mm Hg to give 2-(5-N-t-butylcarbomoyl-2-propoxyphenyl)-8-azapurin-6-one (5.6 g), m.p. 262°–264° C. (with decomposition).

EXAMPLE 9

Compound O

A solution of 2-(5-amino-2-propoxyphenyl)-8-azapurin-6-one (1.5 g) in anhydrous N-methylpyrrolid-2-one (7 ml) was treated with isopropyl isocyanate (0.5 g). The mixture was kept at room temperature overnight and then added to dilute aqueous ammonia solution (50 ml; 2 N). The resulting solution was acidified by treatment with concentrated hydrochloric acid, and the solid which separated was crystallised from methanol to give 2-[2-propoxy-5-(3-isopropylureido)phenyl]-8-azapurin-6-one (1.0 g), in the form of colourless prisms, m.p. 203°–205° C. (with decomposition).

EXAMPLE 10

Compound P

By proceeding in a manner similar to that described in Example 9 but replacing the isopropyl isocyanate used as a starting material by the appropriate quantity of propyl isocyanate, there was prepared 2-[2-propoxy-5-(3-propylureido)phenyl]-8-azapurin-6-one, in the form of light brown crystals recrystallised from a mixture of dimethylformamide and water, m.p. 225°–227° C. (with decomposition).

EXAMPLE 11

Compound Q

By proceeding in a manner similar to that described in Example 9 but replacing the isopropyl isocyanate used as a starting material by the appropriate quantity of methyl isothiocyanate, and keeping the reaction mixture at 100° C. for 2 hours instead of at room temperature overnight, there was prepared 2-[5-(3-methyl-2-thioureido)-2-propoxyphenyl]-8-azapurin-6-one, in the form of a colourless powder, containing water of crystallisation, m.p. 195°–197° C. No recrystallisation was carried out.

EXAMPLE 12

Compound R

By proceeding in a manner similar to that described in Example 11 but replacing the methyl isothiocyanate used as a starting material by the appropriate quantity of propyl isothiocyante, there was prepared 2-[2-propoxy- 5-(3-propyl-2-thioureido)phenyl]-8-azapurin-6-one in the form of a colourless powder, containing water of crystalline, m.p. 199°-200° C.

EXAMPLE 13

Compound S

An intimate mixture of 2-(5-amino-2-propoxyphenyl)-8-azapurin-6-one (2 g) and urea (6 g) was heated at 175° C. for one hour. The mixture was then dissolved in water (50 ml) and the solution was acidified by treatment with concentrated hydrochloric acid. The resulting suspension was heated to boiling point and filtered. The solid was dissolved in dilute aqueous ammonia solution (2 N) and this hot solution was acidified by treatment with concentrated hydrochloric acid. The cooled suspension was filtered to give 2-(2-propoxy-5-ureidophenyl)-8-azapurin-6-one (0.7 g), in the form of a microcrystalline solid, m.p. 264°-268° C. (with decomposition).

EXAMPLE 14

Compound T

A mixture of 2-(5-cyano-2-propoxyphenyl)-8-azapurin-6-one (2.0 g), sodium azide (1.05 g), ammonium chloride (0.9 g) and N-methylpyrrolid-2-one (16 ml) was cautiously heated, with stirring, in a sealed flask for 7 hours at 100°-110° C. The mixture was then cooled and added to water (80 ml) and the mixture was acidified by treatment with concentrated hydrochloric acid. The solid which separated was filtered off and recrystallised from acetic acid to give 2-[2-propoxy-5-(tetrazol-5-yl)phenyl]-8-azapurin-6-one (0.65 g), m.p. 253°-259° C. (with decomposition).

EXAMPLE 15

Compound U

A stirred mixture of 2-(5-amino-2-propoxyphenyl)-8-azapurin-6-one (2.02 g), ethyl 2-ethoxy-1-cyclopentenecarboxylate (1.43 g) and dry sulpholane (20 ml) was heated at 125°-130° C. for 2 hours. The solution was then cooled and poured into dilute hydrochloric acid (200 ml; 2 N) and the yellow solid obtained was filtered off and recrystallised from a mixture of petroleum ether (b.p. 60°-80° C.) and ethyl acetate to give 2-[5-(2-ethoxycarbonylcyclopent-1-enylamino)-2-propoxyphenyl]-8-azapurin-6-one (0.85 g), m.p. 164°-165° C.

EXAMPLE 16

Compounds V and W

A stirred solution of 2-(5-carboxy-2-propoxyphenyl)-8-azapurin-6-one (3 g) in dry dimethylformamide (20 ml) was treated dropwise with thionyl chloride (2.1 ml) at 0° to 5° C. during a period of 10 minutes. The reaction mixture was stirred at 0° to 5° C. for a further period of 24 hours, and then it was treated dropwise with diethylamine (15 ml) over a period of 15 minutes. The mixture was stirred at 0° to 5° C. for a further 2 hours, and then at room temperature for 24 hours. The mixture was poured into water (100 ml) and acidified to pH 1 by treatment with concentrated hydrochloric acid. The resulting white solid was filtered off and purified by applying a chloroform solution of the solid to a column (25 cm×2.5 cm) of silica gel (Kieselgel 60) and eluting with a mixture of chloroform, ethanol and water (380:19:1 v/v). The first product eluted was collected and recrystallised from ethanol to give 2-(5-N,N-diethylcarbamoyl-2-propoxyphenyl)-8-azapurin-6-one (0.9 g), m.p. 199°-201° C. (with decomposition).

By proceeding in a similar manner but replacing the diethylamine used as a starting material by the appropriate quantity of N-methylisopropylamine, there was prepared 2-(5-N-methyl-N-isopropylcarbamoyl-2-propoxyphenyl)-8-azapurin-6-one, m.p. 181.5°-183° C. (with decomposition).

EXAMPLE 17

Compound A (triethanolamine salt)

A suspension of 2-[5-{2,2-bis(ethoxycarbonyl)vinylamino}-2-propoxyphenyl]-8-azapurin-6-one (10.0 g) in dry ethanol (40 ml) was heated at reflux with stirring and was treated gradually with triethanolamine (7.16 g). Heating was continued until a solution was formed. The solution was then cooled and the resulting crystalline solid was filtered off to give the triethanolamine salt of 2-[5-{2,2-bis(ethoxycarbonyl)vinylamino}-2-propoxyphenyl]-8-azapurin-6-one (12.16 g), m.p. 140°-142° C.

EXAMPLE 18

Compound A (triethylamine salt)

A suspension of 2-[5-{2,2-bis(ethoxycarbonyl)vinylamino}-2-propoxyphenyl]-8-azapurin-6-one (10.0 g) in dry isopropanol (40 ml) was heated at reflux with stirring and was treated gradually with triethylamine (4 ml). Heating was continued until a solution was formed. The solution was then cooled and the resulting crystalline solid was filtered off to give the triethylamine salt of 2-[5-{2,2-bis(ethoxycarbonyl)vinylamino}-2-propoxyphenyl]-8-azapurin-6-one (8.15 g). The salt had no melting point but decomposed from 160° C. to 205° C.

REFERENCE EXAMPLE 1

2-(5-Amino-2-propoxyphenyl)-8-azapurin-6-one 2-(5-Nitro-2-propoxyphenyl)-8-azapurin-6-one (32 g) was dissolved in 2-ethoxyethanol (400 ml) and the solution was hydrogenated under a hydrogen pressure of 5 kg/cm$^2$ at 30° C. using platinum oxide (3 g) as catalyst. After 3 hours when reaction was complete, the catalyst was filtered off and the solvent was removed from the filtrate in vacuo. The resulting brown oil was heated at reflux with hydrochloric acid (600 ml; 2 N) and the mixture was then treated with charcoal and filtered. The filtrate was cooled and treated with concentrated aqueous ammonia solution until alkaline, and then was again treated with charcoal and filtered. The filtrate was acidified to pH 4 by treatment with glacial acetic acid and left to stand at 0° C. for 24 hours. The resulting yellow solid was filtered off and recrystallised from ethanol to give 2-(5-amino-2-propoxyphenyl)-8-azapurin-6-one (12.0 g), m.p. 225°-227° C.

The 2-(5-nitro-2-propoxyphenyl)-8-azapurin-6-one, used as starting material, was prepared as follows:

2-(2-Propoxyphenyl)-8-azapurin-6-one (51 g; prepared as described in the specifications of British Pat. No. 1,338,235 and U.S. Pat. No. 3,819,631) was added slowly to stirred concentrated sulphuric acid (300 ml). When all the solid had dissolved, the mixture was cooled to 0° C. and treated slowly with concentrated nitric acid (s.g. 1.42; 14 ml), keeping the temperature at 0° to 5° C.

The resulting dark orange solution was kept at 0°-5° C. for 24 hours and was then poured onto ice (2 kilograms). The solid which precipitated was filtered off and recrystallised from acetone, to give 2-(5-nitro-2-propoxyphenyl)-8-azapurin-6-one (45 g), m.p. 240°–242° C. (with decomposition).

REFERENCE EXAMPLE 2

2-(5-Carboxy-2-propoxyphenyl)-8-azapurin-6-one

A suspension of 2-(5-methyl-2-propoxyphenyl)-8-azapurin-6-one (2.85 g; prepared as described in the specifications of British Pat. No. 1338235 and U.S. Pat. No. 3,819,631) in water (80 ml) was treated with sodium hydroxide (1.0 g). Potassium permanganate (6.3 g) was then added to the resulting solution, and the mixture was stirred and heated at reflux for 150 minutes. The hot mixture was filtered through diatomaceous earth to remove manganese dioxide and the filtrate was acidified with concentrated hydrochloric acid. The solid precipitate was then dissolved in hot aqueous ammonia solution (2 N) and then acidified again with concentrated hydrochloric acid. The resulting hot suspension was then filtered and the white solid formed was washed with water. The solid was treated with ethanol (50 ml) and the resulting suspension was brought to reflux and the 2-(5-carboxy-2-propoxyphenyl)-8-azapurin-6-one (1.8 g), m.p. 271°–272° C. (with decomposition), was filtered off from the hot mixture.

The present invention includes within its scope pharmaceutical compositions which comprise one or more compounds of general formula IV, or a pharmaceutically acceptable salt thereof, together with a pharmaceutical carrier or coating. In clinical practice the compounds of the present invention will normally be administered orally, sub-lingually, nasally, rectally or parenterally.

Solid compositions for oral administration include compressed tablets, pills, dispersible powders, and granules. In such solid compositions the active compound or compounds is or are mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the active compound or compounds with or without the addition of diluents or excipients.

The compound(s) may also be administered sublingually by administration of relatively slowly dissolving tablets which, besides including inert diluents as commonly used in the art, may contain sweetening, flavouring, perfuming and preserving agents.

Solid compositions for rectal administration include suppositories formulated in manner known per se and containing the active compound or compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. Generally the compositions should contain 0.1% to 50% by weight of azapurinone compound, especially when in tablet form. When in aerosol form as hereinafter described the compositions should contain 0.2 to 5%, preferably 2 to 5%, by weight of azapurinone compound.

The active compound or compounds may also be administered by methods known for the inhalation of drugs which are not themselves gaseous under normal conditions of administration. Thus, a solution of the compound or compounds in a suitable pharmaceutically acceptable solvent, for example water, can be nebulized by a mechanical nebulizer, for example a Wright Nebulizer, to give an aerosol of finely-divided liquid particles suitable for administration for inhalation orally or nasally. The solutions may contain stabilizing agents and buffering agents to give an isotonic character, e.g. sodium chloride, sodium citrate and citric acid.

Means for producing self-propelling compositions for generating aerosols for the administration of medicaments are, for example, described in detail in U.S. Pat. Nos. 2,868,691 and 3,095,355.

The compound or compounds may also be administered orally by inhalation in the form of a dry micronised powder, which may be diluted with one or more suitable pharmaceutically acceptable inert solid diluents selected from, for example, lycopodium, boric acid, starch, bismuth subcarbonate and heavy magnesium carbonate.

The pharmaceutical compositions of the present invention may contain, in addition to the compound or compounds of general formula IV, or a pharmaceutically acceptable salt thereof, one or more substances known per se to have bronchodilating actions in man, for example, isoprenaline, salbutamol and prostaglandin $E_1$ ($PGE_1$).

It is highly desirable that the aerosols or micronised powders should have a particle size less than about 10 microns and preferably less than 5 microns, for example, between 0.5 and 3 microns, to ensure effective distribution to very narrow bronchioles. Preferably, administration is by means of devices enabling controlled quantities of the active ingredients to be administered, for example by means of metered valves.

The dose of the compounds of general formula IV employed depends upon the desired therapeutic effect, the route of administration and the duration of the treatment. In the adult, the doses are generally between 0.02 and 1.6 mg/kg body weight per day by administration by inhalation in divided doses, and generally between 4 and 1200, preferably between 4 and 120, mg/kg body weight per day by oral administration.

The following Examples illustrate pharmaceutical compositions according to the present invention:

EXAMPLE 19

Micromilled 2-[5-{2,2-bis(ethoxycarbonyl)-vinylamino}-2-propoxyphenyl]-8-azapurin-6-one (600 mg) and emulsifier YN (150 mg; a mixture of ammonium compounds of phosphatidic acids derived from rape seed oil) were placed in an aluminum vial (20 ml capacity). Trichloromonofluoromethane (2.7 g), dichlorodifluoromethane (9.4 g) and dichlorotetrafluoroethane (4.4 g) were then added, to give a total volume of 12.5 ml. The vial was sealed with a metered valve delivering a dose of 0.05 ml. Each dose (generated from 0.05 ml of suspension) of aerosol released from the pressurised pack thus obtained contained 2.4 mg of 2-[5-{2,2-bis(ethoxycarbonyl)vinylamino}-2-propoxyphenyl]-8-azapurin-6-one.

EXAMPLE 20

Capsules for oral administration were made up in the usual manner by filling No. 2 size gelatine capsules each with 255 mg of the following composition:

| | |
|---|---|
| 2-[5-{2,2-bis(ethoxycarbonyl)vinylamino}-2-propoxyphenyl]-8-azapurin-6-one | 150 mg |
| lactose | 50 mg |
| starch | 50 mg |
| magnesium stearate | 2.5 mg |
| Aerosil | 2.5 mg. |

We claim:
1. An 8-azapurin-6-one of the formula:

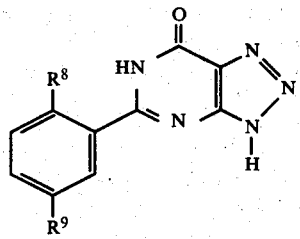

IV wherein $R^8$ represents alkoxy of from 1 to 6 carbon atoms, and $R^9$ represents a group of the formula V, VI, or VIII indicated below:

V   VI

VIII wherein $R^{10}$, $R^{13}$ and $R^{14}$ each represents cyano, or alkanoyl or alkoxycarbonyl of from 2 to 6 carbon atoms, $R^{11}$ represents hydrogen, cyano, or alkanoyl or alkoxycarbonyl of from 2 to 6 carbon atoms, $R^{12}$ represents hydrogen or, when $R^{11}$ represents hydrogen, $R^{12}$ represents alkyl of from 1 to 6 carbon atoms or alkoxycarbonyl of from 2 to 6 carbon atoms, or the pair of symbols $R^{11}$ and $R^{12}$ form together an alkylene chain of the formula $-(C_qH_{2q})-$ wherein q is an integer from 3 to 6, $R^{15}$ represents hydrogen or alkyl of from 1 to 6 carbon atoms, and $Y^1$ represents oxygen or sulphur, and pharmaceutically acceptable salts thereof.

2. An 8-azapurinone according to claim 1 of the formula:

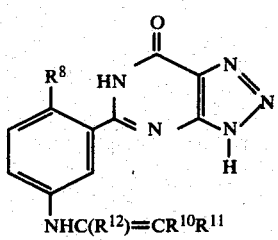

NHC($R^{12}$)=$CR^{10}R^{11}$ wherein $R^8$ is alkoxy of 1 to 6 carbon atoms, $R^{10}$ is cyano, or alkanoyl or alkoxycarbonyl of from 2 to 6 carbon atoms, $R^{11}$ represents hydrogen, cyano, or alkanoyl or alkoxycarbonyl of from 2 to 6 carbon atoms, and $R^{12}$ represents hydrogen or, when $R^{11}$ represents hydrogen, $R^{12}$ represents alkyl of from 1 to 6 carbon atoms or alkoxycarbonyl of from 2 to 6 carbon atoms, or the pair of symbols $R^{11}$ and $R^{12}$ form together an alkylene chain of he formula $-(C_qH_{2q})-$ wherein q is an integer from 3 to 6, and pharmaceutically acceptable salts thereof.

3. An 8-azapurin-6-one according to claim 1 wherein $R^8$ represents methoxy or propoxy, and pharmaceutically acceptable salts thereof.

4. An 8-azapurin-6-one according to claim 2 wherein $R^{10}$ represents cyano, acetyl, methoxycarbonyl or ethoxycarbonyl, $R^{11}$ represents hydrogen, cyano, acetyl, methoxycarbonyl or ethoxycarbonyl, and $R^{12}$ represents hydrogen, or $R^{11}$ represents hydrogen and $R^{12}$ represents methyl or methoxycarbonyl, or the pair of symbols $R^{11}$ and $R^{12}$ together represent a trimethylene group, and pharmaceutically acceptable salts thereof.

5. An 8-azapurin-6-one according to claim 1 wherein $R^9$ represents a group of formula VI in which $R^{13}$ and $R^{14}$ are as defined in claim 2, and pharmaceutically acceptable salts thereof.

6. An 8-azapurin-6-one according to claim 1 wherein $R^9$ represents a group of formula VI in which $R^{13}$ and $R^{14}$ each represents cyano, acetyl, methoxycarbonyl or ethoxycarbonyl, and pharmaceutically acceptable salts thereof.

7. An 8-azapurin-6-one according to claim 1 wherein $R^9$ represents a group of formula VIII in which $R^{15}$ and $Y^1$ are as defined in claim 1, and pharmaceutically acceptable salts thereof.

8. An 8-azapurin-6-one according to claim 1 wherein $R^9$ represents a group of formula VIII in which $R^{15}$ represents hydrogen, methyl, ethyl, propyl, isopropyl or t-butyl, and $Y^1$ is as defined in claim 1, and pharmaceutically acceptable salts thereof.

9. The 8-azapurin-6-one according to claim 2 which is 2-[5-{2,2-bis(ethoxycarbonyl)vinylamino}-2-propoxyphenyl]-8-azapurin-6-one and pharmaceutically acceptable salts thereof.

10. The 8-azapurin-6-one according to claim 2 which is 2-[5-(2,2-diacetylvinylamino)-2-propoxyphenyl]-8-azapurin-6-one and pharmaceutically acceptable salts thereof.

11. The 8-azapurin-6-one according to claim 2 which is 2-[5-(2-cyano-2-ethoxycarbonylvinylamino)-2-propoxyphenyl]-8-azapurin-6-one and pharmaceutically acceptable salts thereof.

12. The 8-azapurin-6-one according to claim 2 which is 2-[5-(2-acetyl-2-ethoxycarbonylvinylamino)-2- propoxyphenyl]-8-azapurin-6-one and pharmaceutically acceptable salts thereof.

13. The 8-azapurin-6-one according to claim 2 which is 2-[5-{2,2-bis(ethoxycarbonyl)vinylamino}-2-methoxyphenyl]-8-azapurin-6-one and pharmaceutically acceptable salts thereof.

14. The 8-azapurin-6-one according to claim 2 which is 2-[5-(2,2-diacetylvinylamino)-2-methoxyphenyl]-8-azapurin-6-one and pharmaceutically acceptable salts thereof.

15. The 8-azapurin-6-one according to claim 2 which is 2-[5-{2,2-bis(methoxycarbonyl)vinylamino}-2-propoxyphenyl]-8-azapurin-6one and pharmaceutically acceptable salts thereof.

16. The 8-azapurin-6-one according to claim 2 which is (Z)-2-[5-{1,2-bis(methoxycarbonyl)vinylamino}-2-propoxyphenyl]-8-azapurin-6-one and pharmaceutically acceptable salts thereof.

17. The 8-azapurin-6-one according to claim 2 which is 2-[5-(1-acetylprop-1-en-2-ylamino)-2-methoxyphenyl]-8-azapurin-6-one and pharmaceutically acceptable salts thereof.

18. The 8-azapurin-6-one according to claim 1 which is 2-[5-(2,4-dioxopent-3ylazo)-2-propoxyphenyl]-8-azapurin-6-one and pharmaceutically acceptable salts thereof.

19. The 8-azapurin-6-one according to claim 1 which is 2-[5-{bis(ethoxycarbonyl)methylazo}-2-propoxyphenyl]-8-azapurin-6-one and pharmaceutically acceptable salts thereof.

20. The 8-azapurin-6-one according to claim 1 which is 2-[2-propoxy-5-(3-isopropylureido)phenyl]-8-azapurin-6-one and pharmaceutically acceptable salts thereof.

21. The 8-azapurin-6-one according to claim 1 which is 2-[2-propoxy-5-(3-propylureido)phenyl]-8-azapurin-6-one and pharmaceutically acceptable salts thereof.

22. The 8-azapurin-6-one according to claim 1 which is 2-[5-(3-methyl-2-thioureido)-2-propoxyphenyl]-8-azapurin-6-one and pharmaceutically acceptable salts thereof.

23. The 8-azapurin-6-one according to claim 1 which is 2-[2-propoxy-5-(3-propyl-2-thioureido)phenyl]-8-azapurin-6-one and pharmaceutically acceptable salts thereof.

24. The 8-azapurin-6-one according to claim 1 which is 2-(2-propoxy-5-ureidophenyl)-8-azapurin-6-one and pharmaceutically acceptable salts thereof.

25. The 8-azapurin-6-one according to claim 2 which is 2-[5-(2-ethoxycarbonylcyclopent-1-enylamino)-2-propoxyphenyl]-8-azapurin-6-one and pharmaceutically acceptable salts thereof.

26. The triethanolamine salt of the 8-azapurin-6-one according to claim 2 which is 2-[5-{2,2-bis(ethoxycarbonyl)vinylamino}-2-propoxyphenyl]-8-azapurin-6-one.

27. The triethylamine salt of the 8-azapurin-6-one according to claim 2 which is 2-5-{2,2-bis(ethoxycarbonyl)vinylamino}-2-propoxyphenyl]-8-azapurin-6-one.

28. A pharmaceutical composition which comprises a 8-azapurin-6-one as claimed in claim 1, or a pharmaceutically acceptable salt thereof, in association with a pharmaceutical carrier or coating.

29. A pharmaceutical composition which comprises an 8-azapurinone as claimed in claim 2 or a pharmaceutically acceptable salt thereof, in association with a pharmaceutical carrier or coating.

30. An 8-azapurin-6-one derivative according to claim 2 wherein $R^8$ represents methoxy or propoxy, and pharmaceutically acceptable salts thereof.

* * * * *